United States Patent [19]

Däahn

[11] 4,205,062
[45] May 27, 1980

[54] PERSPIRATION-INHIBITING SOAPS
[75] Inventor: Günther Dähn, Holzminden, Fed. Rep. of Germany
[73] Assignee: Bayer Atkiengesellschaft, Leverkusen, Fed. Rep. of Germany
[21] Appl. No.: 573,213
[22] Filed: Apr. 30, 1975
[30] Foreign Application Priority Data
May 11, 1974 [DE] Fed. Rep. of Germany ....... 2422903
[51] Int. Cl.² .......................... A61K 7/34; A61K 7/36; A61K 7/38
[52] U.S. Cl. ........................................ 424/66; 424/65; 424/67; 424/68; 252/108
[58] Field of Search ................... 424/65, 66, 67, 68; 252/108
[56] References Cited
U.S. PATENT DOCUMENTS

| | | | |
|---|---|---|---|
| 1,984,669 | 12/1934 | Taub | 424/67 |
| 2,210,013 | 8/1940 | Teller | 424/65 |
| 2,948,684 | 8/1960 | Thiele | 424/65 X |
| 3,152,181 | 10/1964 | Shapiro et al. | 424/67 X |
| 3,235,455 | 2/1966 | Judge et al. | 424/67 X |
| 3,862,305 | 1/1975 | Bouillon et al. | 424/65 X |

FOREIGN PATENT DOCUMENTS

| | | | |
|---|---|---|---|
| 668858 | 8/1963 | Canada | 424/322 |
| 841802 | 2/1939 | France | 424/68 |
| 914736 | 6/1946 | France | 424/68 |
| 368458 | 3/1932 | United Kingdom | 424/68 |

Primary Examiner—Dale R. Ore
Attorney, Agent, or Firm—Sprung, Felfe, Horn, Lynch & Kramer

[57] ABSTRACT

The invention concerns a perspiration-inhibiting soap, a process for its production and body-care preparations containing said soap; the perspiration-inhibiting soap comprising a synthetic washing-active material, a builder, as perspiration-inhibiting agent at least one aluminum salt and/or zinc salt and/or at least one zirconium salt and/or salt of a rare earth element and optionally soap additives known per se.

4 Claims, No Drawings

PERSPIRATION-INHIBITING SOAPS

This invention relates to a perspiration-inhibiting soap, to a process for the production of this perspiration-inhibiting soap and to compositions containing this perspiration-inhibiting soap.

It is already known that active materials which inhibit perspiration, such as aluminum salts, zinc salts, zirconium salts or salts of rare earths, may be incorporated in so-called antiperspirant preparations. Hitherto, preparations of this kind have been used in the form of sprays, sticks, loose powders, compact powders, creams, lotions and roll-ons.

Hitherto, nothing has been known of the use of the aforementioned perspiration-inhibiting active materials in soaps. In the past, it is only so-called deodorant soaps which have been produced on a relatively wide scale. They contain active materials which serve to prevent, eliminate or even to mask odors. So-called deodorant soaps are unable to reduce perspiration. Instead they can only be used to counteract the odors released by the decomposition of perspiration.

There was a serious prejudice against the production and use of soaps which contain perspiration-inhibiting active materials, especially aluminum salts, zinc salts, zirconium salts or salts of rare earths because on the one hand, it is known that the sodium salts of the higher fatty acids which are commonly used as soap preparations are incompatible with salts of polyvalent metals, for example aluminum salts. Substantially insoluble salts of higher fatty acids and polyvalent metals, for example so-called aluminum soaps, are formed in this case. These substantially insoluble salts of higher fatty acids do not have any cleaning effect. In addition, conventional antiperspirant active materials are salts which, when combined with water, can undergo hydrolysis with the result that the pH-value of the water used for washing is reduced. In conventional soap compositions (sodium salts of higher fatty acids), this is known to result in the precipitation of free fatty acids which also deprives the soap of its cleaning effect.

On the other hand, it was assumed that soaps containing perspiration-inhibiting active materials only transfer such small quantities of those active materials to the skin during washing that an adequate perspiration-inhibiting effect cannot be obtained. Furthermore, active materials transferred to the skin by the washing effect of the soap are in danger of being immediately removed again, with the result that an adequate perspiration-inhibiting effect cannot be obtained from the combination of soap plus perspiration-inhibiting active material.

Accordingly, only a few attempts have ever been made to produce perspiration-inhibiting soaps. Thus, DAS No. 1,116,868 describes the production of a perspiration-inhibiting active material consisting of anionic aluminum partly chelated with a hydroxy carboxylic acid. The perspiration-inhibiting active material described in DAS No. 1,116,868 is difficult to produce because the starting materials required for its production have to be mixed within certain narrow limits and reacted under certain reaction conditions which can only be varied within narrow limits. The perspiration-inhibiting active material obtainable in accordance with DAS No. 1,116,868 can be incorporated in conventional soap compositions consisting of fatty acid salts without the precipitation of so-called aluminum soap. However, this active material is preferably incorporated in soap-containing sticks and liquid perspiration-inhibiting preparations.

In addition, DAS No. 1,122,221 describes an antiperspirant stick containing inter alis soap, alcohol and a complex aluminum salt.

According to the two aforementioned publications, aluminum compounds in the form of chelate complexes are used instead of the usual perspiration-inhibiting salts. Unfortunately, these chelate complexes are not as active as the salts.

In addition, Italian Patent Specification No. 481,256 describes a toilet soap which is said to have an inhibiting effect upon the perspiration-producing mechanism of the skin. This effect is said to be produced by the addition of the substances mentioned in that Patent Specification, namely menthol, boric acid, lanolin and vitamin F. However, the conventional perspiration-inhibiting active materials, such as aluminum salts, zinc salts, zirconium salts or salts of rare earths are not used in the soap according to Italian Patent Specification No. 481,256.

Repetition of the procedure described in Italian Patent Specification No. 481,256 has shown that the soap obtained is soft and spongy without any true perspiration-inhibiting effect. This soap was found to have merely a certain, short-lived, cooling effect.

Accordingly, there is still a need for a perspiration-inhibiting soap which is effective and highly compatible and which can be simply produced. It would also be of particular advantage if the aluminum salts, zinc salts, zirconium salts and salts of rare earths known as effective perspiration-inhibiting agents, i.e. a relatively large number of different, readily available perspiration-inhibiting active materials, could be used in this soap.

Accordingly, the present invention relates to a perspiration-inhibiting soap of the kind in question which is distinguished by the fact that it contains synthetic washing-active materials, builders and, as perspiration-inhibiting active materials, aluminum salts, zinc salts, zirconium salts and/or salts of rare earths elements.

The synthetic washing-active materials act as foam-forming and cleaning substances. Any synthetic surfactants may be used for this purpose, although it is preferred to use alkyl sulphates, alkyl aryl sulphonates, alkyl ether sulphates, alkyl sulphonates, sulphosuccinic acid esters, monoesters of fatty acid alkylol amides and fatty alcohols, sulpho fatty acid esters, alkyl naphthalene sulphonate, alkyl phosphate, fatty alcohol polyglycol ethers, fatty acid polyglycol esters, olefin sulphonates, fatty acid acylation products, especially of taurine, methyl taurine, oxethane sulphonic acid and sarcosine, saccharose fatty acid esters, fatty amine derivatives of betaine structure and polypropylene-ethylene glycol condensation products.

It is, of course, also possible to use mixtures of the aforementioned synthetic washing-active materials, providing the individual substances are compatible.

The synthetic washing-active materials are preferably used in quantities of from 40 to 70% by weight and more preferably in quantities of from 50 to 60% by weight, based on the weight of the soap composition as a whole.

The builders serve as supporting materials. Fatty acid esters of polyhydric alcohols, fatty acid alkylol amides, paraffin hydrocarbons, waxes, fatty alcohols, fatty acids, formaldehyde condensation products and/or alkylene oxide adducts may be used for this purpose. The following builders are mentioned by way of example:

ethylene glycol monostearates, ethylene glycol monopalmitates, ethylene glycol distearates, ethylene glycol dipalmitates, propylene glycol monostearates, propylene glycol monopalmitates, propylene glycol distearates, propylene glycol dipalmitates, glycerol monostearates, glycerol monopalmitates, glycerol dipalmitates, glycerol distearates, high molecular weight fatty alcohols, formaldehyde-urea synthetic resins, melamine-formaldehyde condensates paraffinium durum, carnauba wax, bees wax, spermaceti and fatty acid alkylol amides and fatty acids with from 12 to 18 carbon atoms.

It is, of course, also possible to use mixtures of the aforementioned builders. The builders are preferably used in a quantity of from 10 to 30% by weight and more preferably in a quantity of 15 to 20% by weight, based on the soap composition as a whole.

Aluminum salts, zinc salts, zirconium salts or salts of rare earths are used as the perspiration-inhibiting active materials. Examples of suitable perspiration-inhibiting salts are basic aluminum halogenides, especially basic aluminum chlorides e.g. $Al(OH)_2Cl$, $Al_2(OH)_5Cl$ and basic aluminum bromides e.g. $Al(OH)_2Br$, aluminum hydroxide, alum, aluminum acetate, basic aluminum acetate (alumina acetate), aluminum acetotartrate, aluminum formate, aluminum glycinate, aluminum citrate, aluminum dichloraminoacetate, aluminum diethyl malonate, aluminum sulphate, aluminum chloride, aluminum nitrate, aluminum lactate, aluminum phenol sulphonate, aluminum sulphamate, aluminum methionate, aluminum sulphoacetate, aluminum ethane disulphinate, aluminum ethyl sulphate, aluminum sulphobenzoate, aluminum oxyalkyl chlorides, aluminum diisopropyl chloride, aluminum phenol sulphate, zinc phenol sulphonate, zinc methionate, sodium zirconyl acetate, chlorodialuminum zirconate, zirconyl trichloroaluminate, zirconium lactate, praseodymium salts such as praseodymium methionate, and lathanum salts such as lanthanum sulphamate. Particularly suitable perspiration-inhibiting active materials are aluminum hydroxy chloride, zinc phenol sulphonate, aluminum chloride and aluminum acetate. Aluminum hydroxy chloride is particularly preferred. Mixtures of the aforementioned perspiration-inhibiting active materials may also be used.

The perspiration-inhibiting active materials are preferably used in a quantity of from 10 to 30% by weight and more preferably in a quantity of 15 to 20% by weight, based on the weight of the soap composition as a whole.

The perspiration-inhibiting soaps according to the invention may also contain the usual soap additives. For example, drying agents, superfatting agents, plasticizers, lighteners, toning agents, water and/or perfumes. These known soap additives are preferably used in a quantity of from 5 to 35% by weight and more preferably in a quantity of from 10 to 25% by weight based on the weight of the soap composition as a whole.

The drying agents may be added in a quantity of from 0.5 to 2.0% by weight and preferably in a quantity of from 0.5 to 1.0% by weight, based on the weight of the soap composition as a whole. Starches, for example, may be used as the drying agents.

The superfatting agents added may be conventional superfatting agents such as Adeps lanae, vaseline, wool fat alcohols, fatty alcohols, fatty acids, 2-octyl dodecanol, isopropyl myristate, stearate, oleate, lecithins, cholesterol ointment bases such as eucerinum anhydricum, glycerol fatty acid esters and glycol fatty acid esters. Mixtures of these superfatting agents may also be used.

The superfatting agents may be added in a quantity of from 0.5 to 2.5% by weight and preferably in a quantity of from 1 to 2% by weight, based on the weight of the soap compsition as a whole.

Examples of plasticizers which may be added to the soap are polyethylene glycols with molecular weights in the range of from 200 to 1500. The plasticizers are generally used in quantities of from about 3 to 8% by weight and preferably in quantities of from about 4 to 6% by weight, based on the weight of the soap composition as a whole.

The soaps may also contain lighteners and toners, such as titanium dioxide, stilbene derivatives or pyrazoline derivatives. The lighteners and toners may generally be used in quantities of from 0.05 to 0.1% by weight, based on the weight of the soap composition as a whole.

The perspiration-inhibiting soaps may have a water content of from 2 to 12% by weight, preferably from 4 to 10% by weight based on the weight of the soap composition as a whole.

The soaps may be scented with perfumes of the kind normally used for cosmetic purposes providing they are stable with respect to the other substances present in the soap according to the invention, more especially with respect to the particular perspiration-inhibiting agent or agents used. The stability of the perfumes may be determined by known test methods, for example in accordance with Drug and Cosm. Ind. 83/1, pp. 44–45/1-13–114 (1958). Suitable perfumes are, above all, perfumes which are stable in an acid medium, for example anthranilic acid methyl ester, Benzoe-Sumatra resin, ethyl vanillin, cedar wood oil, citronellol, coumarin, dibenzyl ether, diphenyl oxide and heliotropin. Mixtures of perfumes may also be used. The perfumes are generally be used in quantities of from 0.001 to 10% by weight, preferably in quantities of from 0.01 to 5% by weight and, with particular preference, in quantities of from 1 to 2% by weight, based on the weight of the soap composition as a whole.

The invention also relates to the production of a perspiration-inhibiting soap. To this end, a soap is produced by known methods from synthetic, washing-active material, builders, perspiration-inhibiting active materials, consisting of aluminum salts and/or zinc salts and/or zirconium salts and/or salts of rare earths, and optionally other soap additives known per se. For example, the individual components may be mixed at temperatures of from 50° to 80° C. preferably in a heatable kneader at temperatures in the range of from about 65° C. to 70° C. The mixture obtained may then be homogenized, for example on rolls, and subsequently extruded into a strand having a cross-section normally used in soap manufacture. Pieces of soap in the required shape and size are obtained by cutting and molding.

For the individual components of the perspiration-inhibiting soap obtainable in accordance with the invention, the substances described above are used in the quantities described above.

The invention also relates to body-care preparations containing the perspiration-inhibiting soap according to the invention. Preparations of this kind may assume the form of sticks, solutions (lotions), powders, pastes and creams containing the soap according to the invention.

The soaps according to the invention are superior both to conventional deodorant soaps and to the toilet soap described in Italian Patent Specification No. 481,256 because they have a genuine perspiration-inhibiting effect which persists for a longer period. They are also superior to soaps based on sodium salts of higher fatty acids and containing aluminum compounds in the form of chelate complexes as perspiration-inhibiting agents because the active ingredients present in the soaps according to the invention have a better perspiration-inhibiting effect.

The presence in the soap according to the invention of synthetic washing-active materials eliminates all the problems involved in the use of sodium salts of higher fatty acids as washing-active substances.

The soap according to the invention is further distinguished by the fact that it combines a good cleaning effect with a good perspiration-inhibiting effect which, hitherto, had not been considered possible. Conventional perspiration-inhibiting agents do not have any cleaning effect. Accordingly, they have to be used in addition to a conventional soap. By virtue of the soap according to the invention, there is no longer any need to use an additional agent in order to obtain a perspiration-inhibiting effect, but instead it is sufficient to use the soap according to the invention for general washing.

EXAMPLE 1

A mixture of
6.0% by weight of a (6:4)-mixture of glycerol-mono- and di-stearate
1.0% by weight of stearic acid monoethanolamide
2.0% by weight of a (1:1)-mixture of glycol mono- and di-stearate
1.0% by weight of tallow fatty alcohol
1.0% by weight of Adeps lanae anhydricum
20.0% by weight of basic aluminum chloride, $(Al_2(OH)_5Cl \cdot x2H_2O)$ finely ground
6.0% by weight of polyethylene glycol, molecular weight approx. 300
4.0% by weight of distilled water
0.1% by weight of titanium dioxide
38.3% by weight of $C_{12}$–$C_{18}$-alkyl sulphate (sodium salt)
19.6% by weight of the disodium salt of lauric acid ethanolamide sulphosuccinic acid monoester (95%)
1.0% by weight of perfume oil
was mixed in a heatable kneader at a temperature of 65° C. The resulting mixture was homogenized on rolls and extruded into a strand with a cross-section of 4.0 cm. 7.5 cm long pieces were cut from the strand and were molded into soap form.

EXAMPLE 2

A mixture of
6.0% by weight of a (6:4)-mixture of glycerol mono- and di-palmitate
1.2% by weight of stearyl alcohol
2.0% by weight of a (1:1)-mixture of propylene glycol mono- and di-stearate
1.0% by weight of palmitic acid monoethanolamide
19.0% by weight of aluminum phenol sulphonate, finely ground
1.0% by weight of Aleps lanae anhydricum
6.0% by weight of polyethylene glycol, molecular weight approx. 400,
4.5% by weight of distilled water
10.0% by weight of sodium-α-olefin sulphonate ($C_{10}$–$C_{18}$)
29.0% by weight of sodium lauryl sulphate
19.0% by weight of the disodium salt of lauric acid ethanolamide sulphosuccinic acid monoester (95%)
1.0% by weight of maize starch
0.3% by weight of perfume oil
was mixed in a heatable kneader at a temperature of 65° C. The mixture was homogenized on rolls and extruded into a strand with a cross-section of 4 cm. 7.5 cm long pieces were cut from the strand and were molded into soap form.

EXAMPLE 3

A mixture of
6.0% by weight of a (6:4)-mixture of glycerol mono- and di-palmitate
1.2% by weight of stearyl alcohol
2.0% by weight of propylene glycol monostearate
1.0% by weight of palmitic acid monoethanolamide
19.0% by weight of zinc phenol sulphonate, finely ground
1.0% by weight of Aleps lanae anhydricum
6.0% by weight of polyethylene glycol, molecular weight approx. 400,
4.5% by weight of distilled water
10.0% by weight of sodium-α-olefin sulphonate ($C_{10}$–$C_{18}$)
28.0% by weight of sodium lauryl sulphate
19.3% by weight of the disodium salt of lauric acid ethanolamide sulphosuccinic acid monoester (95%)
1.0% by weight of maize starch
1.0% by weight of perfume oil
was mixed in a kneader at a temperature of 65° C. The mixture was homogenized on rolls and extruded into a strand with a cross-section of 4.0 cm. 7.5 cm long pieces were cut from the strand and were molded into soap form.

EXAMPLE 4

A mixture of
20.0% by weight of aluminum hydroxy bromide
1.0% by weight of Adeps lanae anhydricum
0.5% by weight of 2-octyl dodecanol
3.0% by weight of polyethylene glycol, molecular weight approx. 300
3.5% by weight of polyethylene glycol, molecular weight approx. 400
6.0% by weight of distilled water
7.0% by weight of a (6:4)-mixture of glycerol mono- and di-stearate
2.5% by weight of stearic acid monoethanolamide
1.5% by weight of stearic acid
1.0% by weight of bees wax (bleached)
15.0% by weight of N-methyl taurine acylated with a mixture of fatty acids
5.0% by weight of sodium alkyl benzene sulphonate
32.0% by weight of sodium dodecyl benzene sulphonate
2.0% by weight of perfume oil
was mixed in a heatable kneader at a temperature of 65° C. The mixture was homogenized on rolls and extruded into a strand with a cross-section of 4.0 cm. 7.5 cm long pieces were cut from the strand and were molded into soap form.

The soap of Example 1 was used for the tests described in Examples 5 to 8.

EXAMPLE 5

Test for primary irritation:

In an open repetitive irritation test, the soap, in the form of a 10% by weight aqueous solution, was applied once daily over two periods of 5 days to a shaved area of the flank of 20 guinea pigs of an allergizable strain (Pirdright white), each weighing approx. 300 to 500 g, and was rubbed in for about 30 seconds.

Inspection after 2 weeks showed no signs of any skin reactions.

EXAMPLE 6

Test for sensitizing effect:

Using the same animals, local application of the soap was extended to 3 weeks (3 periods of 5 days). After an interval of 5 days, the ensuing reaction was initiated by applying the test substance 3 times to a shaved, untreated area of the neck. Inspection after 24 hours and after 2 and 3 days did not show any sign of skin reaction at the initiation point.

EXAMPLE 7

Epicutaneous skin irritation test:

(a) enclosed pad test:

The perspiration-inhibiting soap, in the form of a 10% by weight solution, was tested among 60 people, including 20 with sensitive skin, by the enclosed epicutaneous pad test described by Jadassohn and Bloch in Dermatologie and Venerologie, Vol. III, p. 458.

The test pads were applied to the back and to the inside of the upper arm, and were covered with plaster to make them airtight.

Inspection after 24 hours and again after 48 and 72 hours did not reveal any signs of skin irritation.

Since the soap was tested in fairly concentrated form under difficult test conditions (covered with moisture sealed in), toxic effects upon the human skin can be ruled out.

(b) repetitive equicutaneous pad test:

The test was carried out among 10 people on the same parts of the body and, after an interval of 24 hours, was repeated 5 times with intervals of 48 hours in between and, finally, was carried out for a seventh time after another interval of 10 days.

Inspection showed no signs of any skin reaction.

EXAMPLE 8

Application test:

20 people with a tendency towards hyperhydrosis on the hands and feet, including 8 with sensitive or allergic skin, used the soap twice daily to wash their hands and feet.

There were no signs of any skin reaction over a 3-week test period. The soap was found to be pleasant and extremely effective in continuous use.

The soap was found to be extremely effective in 5 people suffering from heavy perspiration and in 3 people suffering from moderate perspiration. There was a distinct decrease in perspiration from the hands and feet. 3 people suffering from very heavy perspiration and 5 suffering from moderate perspiration found the soap to be adequate, although not completely effective. The soap was found to be completely ineffective by 2 people in each test group.

We claim:

1. A perspiration-inhibiting soap comprising by weight
   (a) 40 to 70% of a synthetic washing-active material;
   (b) 10 to 30% of a builder;
   (c) 10 to 30% of a perspiration-inhibiting agent of the group consisting of an aluminum salt, a zinc salt, a zirconium salt and a salt of a rare earth element; and
   (d) 5 to 35% of other soap additives known per se.

2. The perspiration-inhibiting soap of claim 1 wherein as perspiration-inhibiting agent (c) there is used a basic aluminum chloride, a basic aluminum bromide, aluminum phenol sulphonate and/or zinc phenol sulphonate.

3. The perspiration-inhibiting soap of claim 1 wherein ingredients (a) to (d) are present in the following percentages by weight based on the weight of the soap composition as a whole:
   (a) 50 to 60%
   (b) 15 to 20%
   (c) 15 to 20%
   (d) 10 to 25%

4. A body-care preparation containing the perspiration-inhibiting soap of claim 1.

* * * * *

UNITED STATES PATENT AND TRADEMARK OFFICE
CERTIFICATE OF CORRECTION

PATENT NO. : 4,205,062
DATED : May 27, 1980
INVENTOR(S) : Gunther Dahn

It is certified that error appears in the above—identified patent and that said Letters Patent is hereby corrected as shown below:

Item (73) "Bayer Atkiengesellschaft, Leverkusen, Fed. Rep, of Germany" should read -- Haarmann & Reimer Gesellschaft mit beschrankter, Haftung, Holzminden, Fed. Rep. of Germany --.

Signed and Sealed this

Twenty-third Day of December 1980

[SEAL]

Attest:

SIDNEY A. DIAMOND

Attesting Officer

Commissioner of Patents and Trademarks